United States Patent [19]

Hsiung et al.

[11] Patent Number: 5,573,928
[45] Date of Patent: Nov. 12, 1996

[54] PORCINE VASOACTIVE INTESTINAL PEPTIDE RECEPTOR AND DNA

[75] Inventors: Hansen M. Hsiung, Carmel; Dennis P. Smith; Xing-Yue Zhang, both of Indianapolis, all of Ind.

[73] Assignee: Eli Lilly and Company, Indianapolis, Ind.

[21] Appl. No.: 112,817

[22] Filed: Aug. 25, 1993

[51] Int. Cl.⁶ ............ C07K 14/705; C12N 15/12; C12N 15/62
[52] U.S. Cl. ............ 435/69.1; 435/64.7; 435/252.3; 435/320.1; 530/350; 536/23.4; 536/23.5
[58] Field of Search ............ 435/69.1, 6, 252.3, 435/320.1, 69.7; 530/350; 536/23.5, 23.4

[56] References Cited

PUBLICATIONS

Sreedharan et al., P.N.A.S. 88:4986–4990, Jun. 1991.
Voisin et al., Life Sciences 48:135–141, 1991.

*Primary Examiner*—John Ulm
*Attorney, Agent, or Firm*—Richard B. Murphy

[57] ABSTRACT

The instant invention provides the porcine pVIP receptor protein. The invention also provides DNA compounds encoding the pVIP receptor, recombinant DNA cloning and expression vectors comprising that DNA, and recombinant host cells comprising those vectors. The invention also provides methods of making the pVIP receptor in recombinant and solid phase systems. The invention also provides methods of using the pVIP receptor in assay systems. The invention also provides methods of using the disclosed DNA sequences as probes to isolate and characterize pVIP receptors and corresponding DNA sequences from other species.

9 Claims, 3 Drawing Sheets

PORCINE VASOACTIVE INTESTINAL PEPTIDE RECEPTOR AND DNA

BACKGROUND OF THE INVENTION

Peptide hormones act as messengers on target tissues stimulating the target organ to respond to a physiological conditions sensed, directly or indirectly, from the brain. A variety of diseases are known to result from abnormalities in the quantity, stability, or activity of indigenously produced peptide hormones. Some types of these diseases are amenable to treatment by hormone supplementation. Peptide hormones, classically isolated from natural sources, are currently produced using recombinant DNA technology making such hormones commercially available for the treatment of a variety of diseases.

The mechanism of action of peptide hormones and their corresponding therapeutic potential cannot be divorced from the complex cascade which mediates their action. Maintenance of the balance between synthesis and catabolism, activation and repression or energy usage and storage allow the organism to adapt to environmental stress but return to a basal state once the stimulus is removed. The instant invention provides a protein, the porcine vasoactive intestinal peptide (pVIP) receptor whose activity is intimately tied to vasodilative effects in lung, gastrointestinal tract and possibly some other tissues.

A number of G-protein coupled receptors have been cloned, for example, the receptors for mouse gonadotropin release hormone (Tsutsumi, et al., 1991, Molecular Endocrinology 6:1163–1169), adenylate cyclase activating polypeptide (Arimura, A., 1992, TEM 3:288–294, lutropin-choriogonadotropin (McFarland, et al., 1989, Science 245:494–499), thyrotropin releasing hormone (Zhao, et al., 1992, Endocrinology 130:3529–3536), human and rat dopamine (Zhou, et al., 1990, Nature 342:76–80), glucagon-like peptide 1 (Thorens 1992, PNAS 89:8641–8645), calcitonin (Lin, et al., 1991, Science 254:1022–1024) parathyroid hormone and parathyroid hormone-related peptide (Abou-Samra, et al., 1992, PNAS 89:2732–2736), endothelin 1 (Lin, et al., 1991 PNAS 88:3185–3189), secretin (Ishihara, et al., 1991, EMBO J. 10:1635–1641), and rat vasoactive intestinal peptide (Ishihara et al., 1992, Neuron 8:811–819).

This invention establishes the precise identity of the porcine pVIP receptor. The present invention also provides methods to purify the pVIP receptor and DNA sequences encoding same, and to produce useful quantities of each using recombinant DNA techniques. This and other objects of the instant invention will be apparent from the specification as a whole.

SUMMARY OF THE INVENTION

The instant invention provides:
(a) the pVIP receptor and functional analogs thereof,
(b) fusion proteins comprising the pVIP receptor or fragments thereof with or without a signal peptide sequence.
(c) DNA sequences encoding the pVIP receptor,
(d) a method for the recombinant production of the pVIP receptor,
(e) recombinant DNA vectors comprising a DNA sequence encoding the pVIP receptor,
(f) transformed host cells useful in the recombinant expression of the pVIP receptor,
(g) a screening system comprising the pVIP receptor useful for determining agents which stimulate or inhibit the action of the pVIP receptor,
(h) a bioactivity assay system comprising eucaryotic host cells expressing the pVIP receptor useful for quantifying the level of stimulation or repression of the pVIP enzymatic activity in response to test compounds
(i) antibodies against the pVIP receptor useful in imaging or diagnostic applications, and
(j) transgenic animals which express the pVIP receptor.

These various aspects of the present invention have been accomplished by the identification and cloning the cDNA sequence encoding the pVIP receptor; incorporating that DNA sequence into a recombinant DNA vector; transforming a suitable host with the vector; expressing the pVIP receptor in such host; and recovering the pVIP receptor so produced. Similarly, the present invention makes it possible to produce the pVIP receptor and analogs thereof by recombinant techniques, as well as providing products and methods related to the pVIP receptor.

BRIEF DESCRIPTION OF THE FIGURES

The restriction site and function maps presented in the accompanying drawings are approximate representations of the recombinant DNA vectors discussed herein. The restriction site information is not exhaustive; therefore there may be more restriction sites of a given type on the vector than are illustrated in the drawings.

MATERIALS

Figure 1:
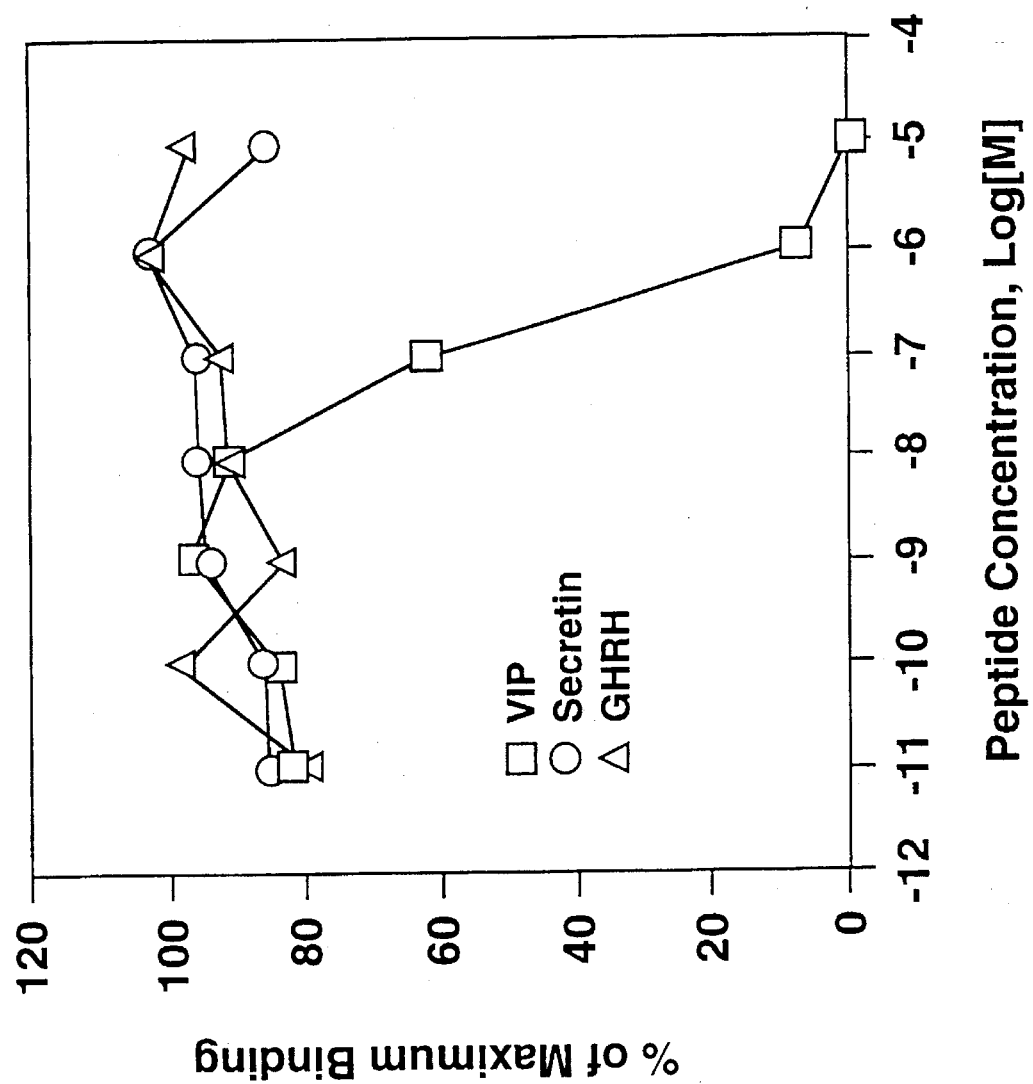
FIG. 1—A radioreceptor assay that shows that the binding specificity of the pVIP receptor. Unlabelled secretin, pVIP, and growth hormone-releasing hormone was used to compete with [$^{125}$I]-VIP binding to pVIP receptor expressing cells.
Figure 2:
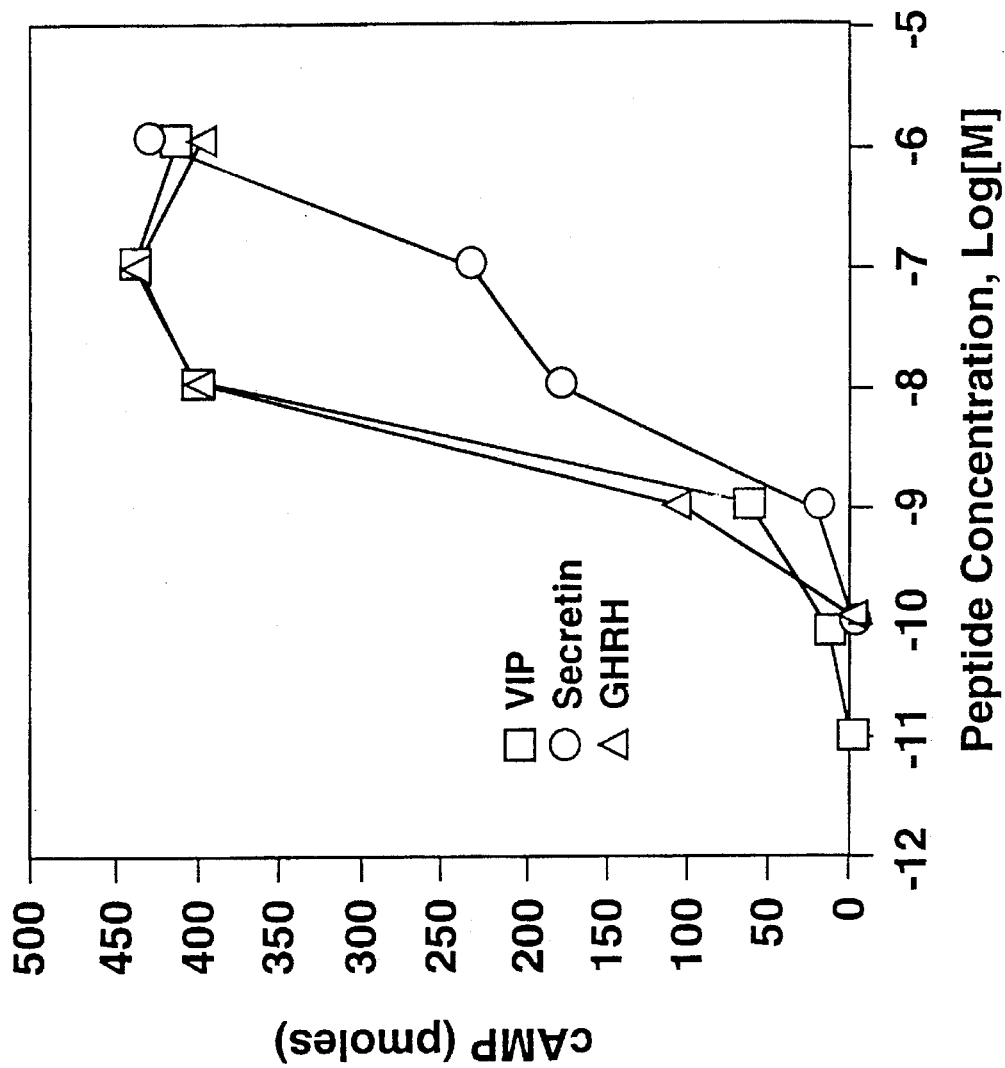
FIG. 2—A graphical representation of the levels of cAMP produced in 293 cells which express the pVIP receptor, 293/vipr, in response to pVIP, GHRH or secretin.
Figure 3:
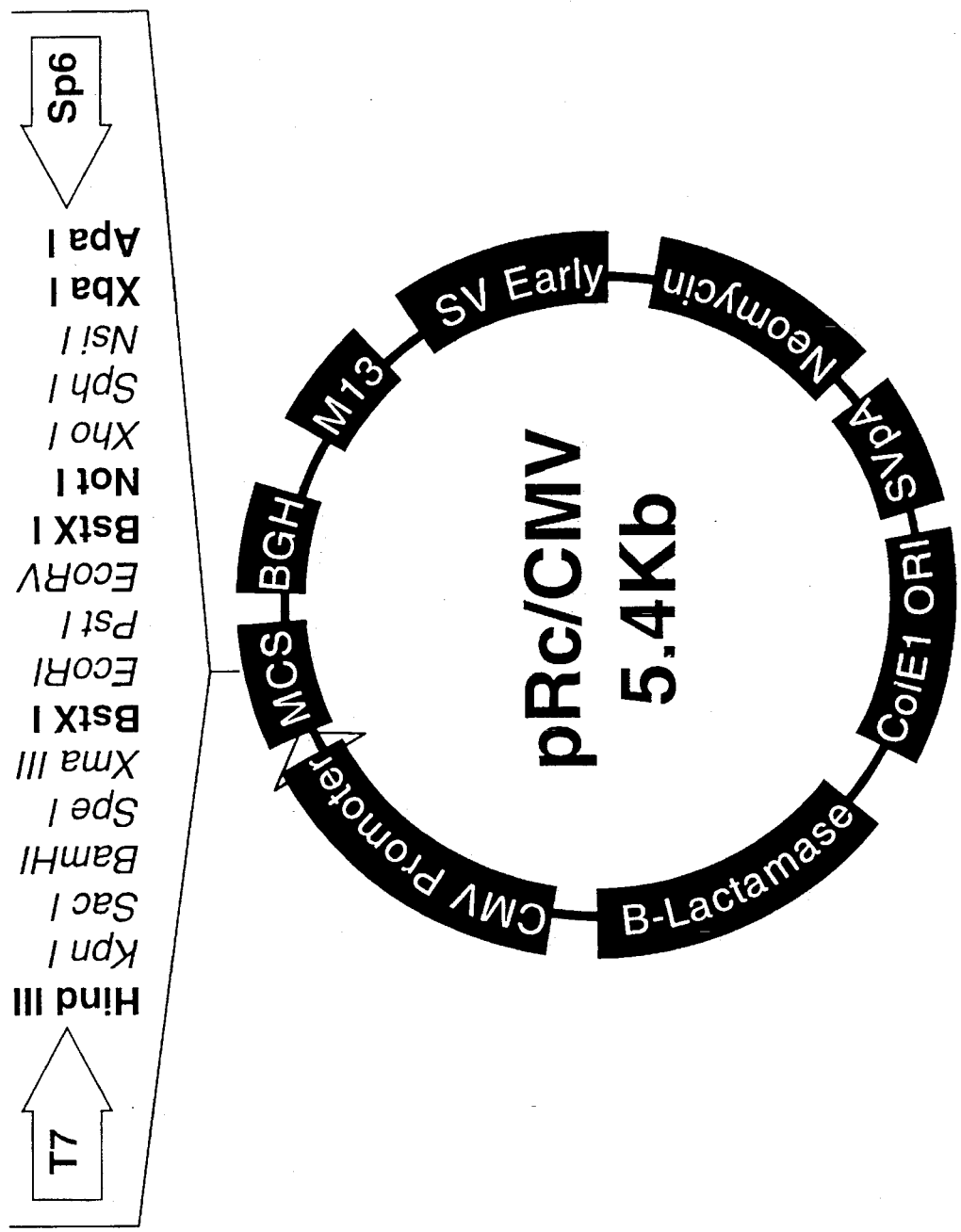
FIG. 3—A restriction site and function map of plasmid pRc/CMV.

Restriction endonucleases and other enzymes (ligase, kinase, phosphatase, polymerases) are commercially available from Boehringer-Mannheim (9115 Hague Road, Indianapolis, IN). Peptide hormones human calcitonin, porcine secretin, porcine vasoactive intestinal polypeptide (VIP), PACAP, GIP, PTH, PHI, PHM are commercially available from Peninsula Laboratories (611 Taylor Way, Belmont, Calif. 94002–4041). [$^{125}$I]VIP is commercially available from Du Pont NEN 549 Albany Street, Boston, Mass. 02118, catalogue no. NEX-192). Antibiotic Geneticin G-418 is commercially available from Gibco-BRL. Liquid nitrogen-frozen porcine tissues used for RNA isolation were obtained from Pel-Freez, 205 N. Arkansas, P.O. Box 68, Rogers Ark. 72757.

DEFINITIONS

For purposes of the present invention as disclosed and claimed herein, the following terms are defined as follows:

Analog—a compound which is structurally similar to another. When used in reference to polypeptides it refers to primary, secondary, or tertiary structure.

Base pair (bp)—refers to DNA or RNA. The abbreviations A,C,G, and T correspond to the 5'-monophosphate forms of the nucleosides (Deoxy)adenosine, (deoxy) cytidine, (deoxy)guanosine, and (deoxy)thymidine, respectively, when they occur in DNA molecules. The abbreviations U,C,G, and T correspond to the 5'-monophosphate forms of the nucleosides uridine, cytidine, guanosine, and thymidine, respectively when they occur in RNA molecules. In double stranded DNA, base pair may refer to a partnership of A with T or C with G. In a DNA/RNA, heteroduplex base pair may refer to a partnership of T with U or C with G.

Control region—refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly $A^+$ tail to the 3' end of the transcribed mRNA.

Dephosphorylation—refers to the removal of the N-terminal 5' phosphates by treatment with bacterial alkaline phosphatase (BAP) or calf intestinal alkaline phosphatase (CIAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T, et al., Molecular Cloning pp. 133–134 (1982).

Digestion—of DNA refers to catalytic cleavage of the DNA with a restriction enzyme that acts only at certain sequences in the DNA. The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer.

Filling or blunting—the procedures by which the single stranded end in the cohesive terminus of a restriction enzyme-cleaved nucleic acid is converted to a double strand. This procedure eliminates the cohesive ("sticky") end and forms a blunt end. This process is used to convert a restriction-cut end that may be cohesive with a terminus compatible with any blunt-cutting restriction endonuclease or other filled cohesive terminus. Typically, blunting or filling is achieved by the use of the Klenow fragment of DNA polymerase I by procedures well known in the art.

Functional analog—refers to a molecule having similar functional properties but a modified structure relative to the naturally occurring form of that molecule or compound. Functional analogs include fragments of (or additions to) the parent molecule having similar functional properties and reactivities as the parent molecule.

Ligation—refers to the process of forming phosphodiester bonds between two double stranded nucleic acid fragments (Maniatis, T. et al., Id., p. 146). Unless otherwise provided, ligation may be accomplished using known buffers and conditions with T4 DNA ligase.

Milli-Q® water—water purified through the Milli-Q® filtration system available from Millipore Corporation, Ashby Road, Bedford, Mass. 01730.

Oligonucleotides—refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

Plasmid—a extrachromosomal self-replicating genetic element. Plasmids are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

Reading frame—the nucleotide sequence from which translation occurs "read" in triplets by the translational apparatus of tRNA and ribosomes and associated factors each triplet corresponding to a particular amino acid. Because each triplet is distinct and of the same length, the coding sequence must be a multiple of three, a base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

Recombinant DNA Cloning Vector—any autonomously replicating agent, including, but not limited to, plasmids and phages, comprising a DNA molecule to which one or more additional DNA segments can or have been added.

Recombinant DNA Expression Vector—any recombinant DNA cloning vector in which a promoter has been incorporated.

Replicon—a DNA sequence that controls and allows for autonomous replication of a plasmid or other vector.

RP-HPLC—an abbreviation for reverse-phase high performance liquid chromatography.

Transcription—the process whereby information contained in a nucleotide sequence of DNA is transferred to a complementary RNA sequence.

Transfection—refers to the taking up of an expression vector by a host cell whether or not any coding sequences are in fact expressed. Numerous methods of transfection are known to the ordinarily skilled artisan, for example, CaPO4 and electropotation. Successful transfection is generally recognized when any indication of the operation of this vector occurs within the host cell.

Transformation—means introducing DNA into an organism so that the DNA is replicable, either as an extrachromosomal element or by chromosomal integration. Transformation may be achieved by the method of Graham, F. and van der Eb, A, (1973) Virology 52:456–7. Other methods such as nuclear injection, protoplast fusion or by calcium treatment using calcium chloride as described by Cohen, S. N. et al., (1972) Proc. Natl. Acad. Sci. (USA) 69:21.

Translation—the process whereby the genetic information of messenger RNA is used to specify and direct the synthesis of a polypeptide chain.

Vector—a replicon used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors, since they are replicons in their own right. Artificial vectors are constructed by cutting and joining DNA molecules from different sources using restriction enzymes and ligases. The term "vector" as used herein includes Recombinant DNA cloning vectors and Recombinant DNA expression vectors.

DETAILED DESCRIPTION OF THE INVENTION

The instant invention provides:
(a) the pVIP receptor and functional analogs thereof,
(b) fusion proteins comprising the pVIP receptor or fragments thereof with or without a signal peptide sequence.
(c) DNA sequences encoding the pVIP receptor,
(d) a method for the recombinant production of the pVIP receptor,
(e) recombinant DNA vectors comprising a DNA sequence encoding the pVIP receptor,
(f) transformed host cells useful in the recombinant expression of the pVIP receptor,
(g) a screening system comprising the pVIP receptor useful for determining agents which stimulate or inhibit the action of the pVIP receptor,
(h) a bioactivity assay system comprising eucaryotic host cells expressing the pVIP receptor useful for quantifying the level of stimulation or repression of the pVIP enzymatic activity in response to test compounds
(i) antibodies against the pVIP receptor useful in imaging or diagnostic applications, and
(j) transgenic animals which express the pVIP receptor.

A cDNA sequence encoding the pVIP receptor protein including the endogenous signal peptide sequence was isolated from a total porcine mRNA library and comprises the DNA sequence: [Sequence ID#1]

```
ATG CGC CCC CTG AGC CCG CCG CCG GCC GGC TGG TTC TGC
GTG CTG GCC GGC GTC CTC GCC TGT GTC CTC GGC CCC GTG
GGC AGC TGG GCA GTC GGG TTG CAG CAG GAG GAG TGT GAC
TAT CTG CAG ATG ATC AAG GTA CAG CAC AAG CAG TGC CTG
GAG GAA GCC CAG CTG GAG AAT GAA ACA TCA GGC TGC AGC
AAG ATG TGG GAC AAC CTC ACC TGC TGG CCA GCC ACC CCT
CGG GGA CAG GTG GTT GTC TTA GCT TGC CCT CTC ATC TTT
AAG CTC TTC TCT CCC ACT CAA GGC CTC AAC GTG AGC CGC
AAC TGC ACA GAC GAG GGC TGG ACG CCC CTG GAG CCT GGC
CCC TAC CCC ATT GCC TGT GGC ATG GAT GAC AAG GCA TCG
GGT TTG GAC GAG CAG CAG ACA GTG TTC TAC AAT TCT GTG
AAG ACC GGC TAC ACC ATC GGC TAC AGC TTG TCC CTC GCC
GCC CTC CTG GTC GCC ACC GCC ATC TTG AGC CTG TTC AGG
AAG CTC CAC TGC ACT CGG AAC TAC ATC CAC ATG CAC CTC
TTC ATA TCC TTC ATC CTG AGG GCC ACC GCC GTC TTC ATC
AAA GAC TTG GCC CTC TTC GAC AGC GAG GAA TCA GAC CAC
TGC TCC AAG GGC TCG GTG GGC TGT AAG GCA GCC GTG GTT
TTA TTC CAG TAC TGT GTC ATG GCC AAC TTC TTC TGG CTG
CTG GTG GAG GGC CTC TAC CTG CAC ACC CTA CTT GCC GTG
TCC TTC TTC TCT GAG CGG AAG TAC TTC TGG GGG TAC ATA
TTC GTC GGC TGG GGG GTG CCC AGC ACC TTC ATC ATG GTG
TGG ACC GTC GTC AGA ATC CAT TTT GAG GAT TAT GGA TGC
TGG GAC ACC ATC CAC TCC TCA CTG TGG TGG ATC ATA AAG
GCC CCC ATC CTC GCC TCC ATC CTG GTG AAC TTC ATC CTA
TTC ATT CGC ATC ATC GGA ATC TTG GTT CAG AAA CTG CGA
CCC CCA GAT GTC GGG AAG AGT GAC AAC AGC CCA TAC TCG
AGA CTA GCC AAG TCC ACT CTT CTG ATC CCC CTA TTT
GGA GTG CAC TAC ATC ATG TTT GCC TTC TTC CCT GAC AAT
TTT AAG GCC GAA GTG AAA ATG GTC TTT GAG CTC ATC GTG
GGA TCT TTC CAG GGT TGT GTG GTG GCC ATC CTC TAC TGC
TTC CTC AAT GGT GAG GTG CAG GCA GAG CTG CGG CGG AAG
TGG CGG CGC TGG CAC CAG CAG GGC GTC TTG GGC TGG GAC
TCC AAA TAC CAG CAC CCG TCA GGA GGC AGC AAC GGG GAC
ACG TGC AGC ACG CAG GTC TCC ATG CTG ACC CGT GTC AGC
CCC AGT GCG CGC CGC TCC TCC AGC TTC CAG GCC GAA GTC
TCC CTG GTC TGA
```

The identity of the protein encoded by the above DNA was demonstrated by recombinant expression of the sequence in a eucaryotic cell and subsequent demonstration of pVIP receptor activity. Briefly, a double stranded counterpart to Sequence ID#i, externally modified to incorporate convenient restriction sites, was integrated into the pRc/CMV vector and recombinantly expressed in 293 cells. The cDNA transcript included the signal peptide region of the native transcript facilitating proper orientation and integration into the transfected cell membrane. Exposure of the transfected 293 cells expressing the protein of Sequence ID#2 on the cell surface demonstrated an intracellular increase in cAMP levels upon exposure to VIP. The cAMP level was also measured upon exposure of the transfected cells in response to the addition of secretin, and GHRH, two peptides closely related to VIP. The levels of cAMP produced by the exposure of the transfected cells expressing the protein of Sequence ID#2 to VIP, GHRH and secretin are shown in Table 1 below.

TABLE 1

| Exposure of 293/VIPR cells to VIP | |
|---|---|
| [VIP]* | intracellular [cAMP]** |
| $10^{-11}$ | <10 |
| $10^{-10}$ | 15 |

TABLE 1-continued

Exposure of 293/VIPR cells to VIP

| | intracellular [cAMP]** |
|---|---|
| $10^{-9}$ | 64 |
| $10^{-8}$ | 404 |
| $10^{-7}$ | 440 |
| $10^{-6}$ | 420 |
| [GHRH] | |
| $10^{-11}$ | <10 |
| $10^{-10}$ | <10 |
| $10^{-9}$ | 105 |
| $10^{-8}$ | 400 |
| $10^{-7}$ | 404 |
| $10^{-6}$ | 400 |
| [secretin] | |
| $10^{-11}$ | <10 |
| $10^{-10}$ | <10 |
| $10^{-9}$ | 28 |
| $10^{-8}$ | 185 |
| $10^{-7}$ | 240 |
| $10^{-6}$ | 440 |

*hormone concentration is expressed in molarity
**intracellular cAMP is expressed in pmoles/$10^5$ cells The invention further provides the pVIP receptor and functional analogs thereof. Functional analogs typically exhibit the same qualitative biological activity as the naturally-occurring analog, although functional analogs also are selected in order to modify the characteristics of pVIP receptor. Functional analogs are ordinarily engineered variations, but such functional analogs include naturally occurring allelic or interspecies variations of the pVIP receptor amino acid sequences.

The functional analogs ordinarily are prepared by modification of the DNA encoding the pVIP receptor and thereafter expressing the DNA in recombinant cell culture. Techniques for making substitutional mutations at predetermined sites in DNA having a known sequence are well known, for example M13 primer mutagenesis. The mutations that might be made in the DNA encoding the functional analog pVIP receptor must not place the sequence out of reading frame and preferably will not create complementary regions that could produce secondary mRNA structure (EP 75,444A).

Functional analogs of the pVIP receptor are generally created by modification of the amino acid sequence of the protein in a specific and limited manner. While the site for introducing an amino acid sequence variation is predetermined, the mutation per se need not be predetermined. For example, in order to optimize the performance of a mutation at a given site, random mutagenesis may be conducted at the target codon or region and the expressed pVIP receptor functional analogs screened for the optimal combination of desired activity.

Functional analogs of the pVIP receptor are typically generated by deletion, insertion, or substitutions of a single (or few) amino acid residues. Such modifications generally are made in accordance with the following Table V to produce functional analogs of the pVIP receptor.

TABLE V

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those in Table V, i.e., selecting residues that differ more significantly in their effect on maintaining (a) secondary or tertiary structure of the polypeptide backbone, (b) the charge or hydrophobicity of the residue, or (c) the bulk of the side chain. The substitutions which in general are expected to produce the greatest changes in pVIP receptor properties will be those in which (a) a hydrophilic residue is substituted by a hydrophobic residue; (b) a cysteine or proline is substituted for any other residue; (c) a residue having a positive charged side chain is substituted for a negatively residue; or (d) a residue having a bulky side chain is substituted for one not having a side chain.

Site specific mutagenesis may also be employed to eliminate N- or O-linked glycosylation sites resulting in non-glycosylated functional analogs of the pVIP receptor. The non-glycosylated pVIP receptor may be recombinantly produced in prokaryotic cell culture. Deletions of cysteine or other labile residues also may be desirable, for example in increasing the oxidative stability of the pVIP receptor. Deletions or substitutions of potential proteolysis sites, e.g. Arg-Arg, may also be accomplished by deleting one of the basic residues or substituting one by glutaminyl or histidinyl residues.

A preferred pVIP receptor encoded by Sequence ID#1 containing the endogenous signal peptide possesses the amino acid sequence: [Sequence ID#2]

Met—Arg—Pro—Leu—Ser—Pro—Pro—Pro—Ala—Gly—Trp—Phe—Cys—
Val—Leu—Ala—Gly—Val—Leu—Ala—Cys—Val—Leu—Gly—Pro—Val—
Gly—Ser—Trp—Ala—Val—Gly—Lys—Gln—Cys—Leu—Glu—Glu—Ala—
Gln—Leu—Glu—Asn—Glu—Thr—Ser—Gly—Cys—Ser—Lys—Met—Trp—
Asp—Asn—Leu—Thr—Cys—Trp—Pro—Ala—Thr—Pro—Arg—Gly—Gln—
Val—Val—Val—Leu—Ala—Cys—Pro—Leu—Ile—Phe—Lys—Leu—Phe—
Ser—Pro—Thr—Gln—Gly—Leu—Asn—Val—Ser—Arg—Asn—Cys—Thr—
Asp—Glu—Gly—Trp—Thr—Pro—Leu—Glu—Pro—Gly—Pro—Tyr—Pro—
Ile—Ala—Cys—Gly—Met—Asp—Asp—Lys—Ala—Ser—Gly—Leu—Asp—

-continued

```
Glu—Gln—Gln—Thr—Val—Phe—Tyr—Asn—Ser—Val—Lys—Thr—Gly—
Tyr—Thr—Ile—Gly—Tyr—Ser—Leu—Ser—Leu—Ala—Ala—Leu—Leu—
Val—Ala—Thr—Ala—Ile—Leu—Ser—Leu—Phe—Arg—Lys—Leu—His—
Cys—Thr—Arg—Asn—Tyr—Ile—His—Met—His—Leu—Phe—Ile—Ser—
Phe—Ile—Leu—Arg—Ala—Thr—Ala—Val—Phe—Ile—Lys—Asp—Leu—
Ala—Leu—Phe—Asp—Ser—Glu—Glu—Ser—Asp—His—Cys—Ser—Lys—
Gly—Ser—Val—Gly—Cys—Lys—Ala—Ala—Val—Val—Leu—Phe—Gln—
Tyr—Cys—Val—Met—Ala—Asn—Phe—Phe—Trp—Leu—Leu—Val—Glu—
Gly—Leu—Tyr—Leu—His—Thr—Leu—Leu—Ala—Val—Ser—Phe—Phe—
Ser—Glu—Arg—Lys—Tyr—Phe—Trp—Gly—Tyr—Ile—Phe—Val—Gly—
Trp—Gly—Val—Pro—Ser—Thr—Phe—Ile—Met—Val—Trp—Thr—Val—
Val—Arg—Ile—His—Phe—Glu—Asp—Tyr—Gly—Cys—Trp—Asp—Thr—
Ile—His—Ser—Ser—Leu—Trp—Trp—Ile—Ile—Lys—Ala—Pro—Ile—
Leu—Ala—Ser—Ile—Leu—Val—Asn—Phe—Ile—Leu—Phe—Ile—Arg—
Ile—Ile—Gly—Ile—Leu—Val—Gln—Lys—Leu—Arg—Pro—Pro—Asp—
Val—Gly—Lys—Ser—Asp—Asn—Ser—Pro—Tyr—Ser—Arg—Leu—Ala—
Lys—Ser—Thr—Leu—Leu—Leu—Ile—Pro—Leu—Phe—Gly—Val—His—
Tyr—Ile—Met—Phe—Ala—Phe—Phe—Pro—Asp—Asn—Phe—Lys—Ala—
Glu—Val—Lys—Met—Val—Phe—Glu—Leu—Ile—Val—Gly—Ser—Phe—
Gln—Gly—Cys—Val—Val—Ala—Ile—Leu—Tyr—Cys—Phe—Leu—Asn—
Gly—Glu—Val—Gln—Ala—Glu—Leu—Arg—Arg—Lys—Trp—Arg—Arg—
Trp—His—Gln—Gln—Gly—Val—Leu—Gly—Trp—Asp—Ser—Lys—Tyr—
Gln—His—Pro—Ser—Gly—Gly—Ser—Asn—Gly—Asp—Thr—Cys—Ser—
Thr—Gln—Val—Ser—Met—Leu—Thr—Arg—Val—Ser—Pro—Ser—Ala—
Arg—Arg—Ser—Ser—Ser—Phe—Gln—Ala—Glu—Val—Ser—Leu—Val
```

The pVIP receptor cDNA is characterized by the presence of a DNA sequence encoding a signal (or leader) polypeptide which serves to direct the ultimate location of the protein in the cell membrane. Generally, signal peptides are proteolytically cleaved from a residual protein as part of the secretory process in which the protein is transported into the host cell periplasm or culture medium. However, the functional pVIP receptor may include the signal peptide in its primary sequence yet retain pVIP binding activity. Analogs of the pVIP receptor incorporating modified signal peptides are within the scope of the present invention.

It is well known in the art that signal peptides facilitate the extracellular discharge of secretory proteins in both prokaryotic and eukaryotic environments. It has been shown that the addition of a heterologous signal peptide to a normally cytosolic protein will result in the extracellular transport of the normally cytosolic protein in E. coli. MacIntyre, et al.,(1987) J. Biol. Chem., 262:8416–8422. It is well known in the art that alternate signal peptide sequences may function with heterologous coding sequences. For instance, a DNA sequence encoding the signal peptide from another receptor such as the secretin receptor may be substituted for the DNA sequence encoding the signal peptide of the pVIP receptor resulting in a heterologous protein retaining pVIP receptor characteristics. The recombinant production of such fusion proteins maybe accomplished by the addition of a DNA sequence encoding a signal peptide appropriate to the host organism inserted 5' to, and in reading frame with, the protein coding sequence.

Signal peptides are well known in the art which could be similarly incorporated into the pVIP structure to make other functional analogs of the pVIP receptor. The signal peptide may be microbial or mammalian, but is preferably is mammalian. In the preferred practice of the invention the signal peptide used is a signal peptide native to a secretory protein of the host cell line. In the most preferred practice of the invention as exemplified herein, the signal peptide is the native pVIP receptor presequence.

Furthermore, the signal sequence may be wholly synthetic. Synthetic "idealized" signal peptides have been shown to function in both prokaryotic and eukaryotic environments. von Heijne, G. (1990) J. Membrane Biol., 115: 195–201. The principles of signal peptides are similar in both prokaryotic and eukaryotic organisms. Both prokaryotic and eukaryotic signal peptides possess an overall three domain structure and with no precise sequence conservation necessary to preserve function. von Heijne, G., supra. Generally, the presence of basic and/or charged amino acid residues near the amino terminus of the structural protein inhibits secretion. Yamane, K., et al. (1988) J. Biol. Chem., 263:19690–19696, Summers, R. G., et al. (1989) J. Biol. Chem., 264:20082–20088. In order to insure the efficient cleavage of the signal peptide from the fusion protein construct, it is desirable to maintain the nature of the amino acid sequence at the interface between the signal peptide and the coding sequence of the mature art protein. Conservation of charge and hydrophobicity and the elimination of charged residues immediately downstream of the signal peptide cleavage point are generally important to efficient translocation. However, it is not critical that any one particular amino acid sequence be maintained.

The invention further provides transgenic animals produced using the pVIP coding sequence or DNA sequences encoding functional analogs of the pVIP useful as research tools in the study of pVIP activity. Construction of transgenic animals which express heterologous foreign proteins is well known in the art. See Wagner, et al (U.S. Pat. No. 4,873,191 issued Oct. 10, 1989), Evans, et al. (U.S. Pat. No. 4,870,009 issued Sep. 26, 1989) the entire teachings of which are hereby incorporated by reference, Cline, et al (1980) Nature, 284:422–425, and Capecchi M. R. (1980) Cell, 22:479–488.

The invention also provides methods of making pVIP receptor. The compounds of the present invention may be produced either by recombinant DNA technology or well known chemical procedures, such as solution or solid-phase peptide synthesis, or semi-synthesis in solution beginning with protein fragments coupled through conventional solution methods.

The synthesis of the pVIP receptor or fragments thereof may proceed by solid phase peptide synthesis or by recombinant methods. The principles of solid phase chemical synthesis of polypeptides are well known in the art and may be found in general texts in the area such as Dugas, H. and Penney, C., Bioorganic Chemistry (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City California) and synthesis cycles supplied by Applied Biosystems. Boc amino acids and other reagents are commercially available from Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asparagine, Glutamine, and Arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Boc deprotection may be accomplished with trifluoroacetic acid (TFA) in methylene chloride. Following completion of the synthesis the peptides may be deprotected and cleaved from the resin with anhydrous hydrogen fluoride containing meta-cresol. Cleavage of the side chain protecting group(s) and of the peptide from the resin is carried out at zero degrees Centigrade or below, preferably −20° C. for thirty minutes followed by thirty minutes at 0° C. After removal of the HF, the peptide/resin is washed with ether, and the peptide extracted with glacial acetic acid and lyophilized. Purification is accomplished by size-exclusion chromatography on a Sephadex G-10 (Pharmacia) column in 10% HOAc.

The pVIP receptor may also be produced by recombinant methods. Recombinant methods are preferred if a high yield is desired. The basic steps in the recombinant production of pVIP receptor include:

a) construction of a synthetic or semisynthetic (or isolation from natural sources) a DNA encoding the pVIP receptor, b) integrating the coding sequence into an expression vector in a manner suitable for the expression of the pVIP receptor either alone or as a fusion protein, c) transforming an appropriate eukaryotic or prokaryotic host cell with the expression vector, and d) recovering and purifying the recombinantly produced pVIP receptor.

As previously stated, the coding sequence may be wholly synthetic, semi-synthetic or the result of modification of the native pVIP receptor cDNA. The pVIP receptor cDNA isolated in substantial accordance with the teaching of the examples herein comprises the DNA sequence of Sequence ID#1.

Synthetic genes, the in vitro or in vivo transcription and translation of which will result in the production of pVIP receptor may be constructed by techniques well known in the art. Owing to the natural degeneracy of the genetic code, the skilled artisan will recognize that a sizable yet definite number of DNA sequences may be constructed which encode pVIP receptor. In the preferred practice of the invention, synthesis of the pVIP receptor is achieved by recombinant DNA technology.

The gene encoding the pVIP receptor may be created by synthetic methodology. Such methodology of synthetic gene construction is well known in the art. Brown, et al. (1979) *Methods in Enzymology,* Academic Press, N.Y., Vol. 68, pgs. 109–151. The DNA sequence corresponding to the synthetic pVIP receptor gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

It may be desirable in some applications to modify the coding sequence of the pVIP receptor relative to the native protein so as to incorporate a convenient protease sensitive cleavage site, e.g., between the signal peptide and the structural protein facilitating the controlled excision of the signal peptide from the fusion protein construct.

The pVIP receptor may be made either by direct expression or as fusion protein comprising the pVIP receptor followed by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., Carter P. site specific Proteolysis of Fusion Proteins, Ch. 13 in *Protein Purification: From Molecular Mechanisms to Large Scale Processes*, American Chemical Soc., Washington, D.C. (1990).

Construction of suitable vectors containing the desired coding and control sequences employ standard ligation techniques. Isolated plasmids or DNA fragments are cleaved, tailored, and religated in the form desired to form the plasmids required.

In general, procaryotes are used for cloning of DNA sequences in constructing the vectors useful in the invention. For example, *E. coli* K12 strain 294 (ATCC No. 31446) is particularly useful. Other microbial strains which may be used include *E. Coli* B and *E. coli* X1776 (ATCC No. 31537). These examples are illustrative rather than limiting.

To effect the translation of the desired pVIP receptor or analog, one inserts the engineered synthetic DNA sequence in any of a plethora of appropriate recombinant DNA expression vectors through the use of appropriate restriction endonucleases. The pVIP receptor is a relatively large protein. A synthetic pVIP receptor coding sequence is designed to possess restriction endonuclease cleavage sites at either end of the transcript to facilitate isolation from and integration into these expression and amplification and expression plasmids. The isolated cDNA pVIP receptor coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the pVIP receptor coding sequence with control sequences to achieve proper in-frame reading and expression of the pVIP receptor.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., Gene 2:95 [1977]), pBR322 contains genes for ampicillin and tetracycline resistance and Thus provides easy means for identifying transformed cells.

The pBR322 plasmid, or other microbial plasmid must also contain or be modified to contain promoters and other control elements commonly used in recombinant DNA construction.

The pVIP receptor coding sequence must be positioned so as to be in proper reading frame with the promoter and ribosome binding site of the expression vector, both of which are functional in the host cell in which the pVIP receptor is to be expressed. In the preferred practice of the invention, the promoter-operator region is placed in the same sequential orientation with respect to the ATG start codon of DNA sequence encoding the protein of Sequence ID#2 as the promoter-operator occupies with respect to the ATG-start codon of the gene from which it was derived. Synthetic or modified promoter-operator regions such as the tac promoter are well known in the art. When employing such synthetic or modified promoter-operator regions they should be oriented with respect to the ATG start codon of the pVIP receptor coding sequence as directed by their creators.

The pVIP receptor or analogs may be recombinantly produced in eukaryotic expression systems. General principles involved in the recombinant expression of receptors is described in "Expression of receptor genes in cultured cells" Ch. 11 of *receptor Biochemistry: A Practical Approach*, edited by E. C. Hulme IRL Press, Oxford University Press, Walton St. Oxford OX2 6DP, England.

Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., (1978) *Nature*, 273:113. The entire SV40 genome may be obtained from plasmid pBRSV, ATCC 45019. The immediate early promoter of the human cytomegalovirus may be obtained from plasmid pCMBβ (ATCC 77177). Of course, promoters from the host cell or related species also are useful herein.

Transcription of a DNA encoding pVIP receptor by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 5' (Laimins, L. et al., [1981] PNAS 78:993) and 3' (Lusky, M. L., et al., [1983] *Mol. Cell Bio.*, 3:1108) to the transcription unit, within an intron (Banerji, J. L. et al., [1983] *Cell*, 33:729) as well as within the coding sequence itself (Osborne, T. F., et al., [1984] Mol. Cell Bio. 4:1293). Many enhancer sequences are now known from mammalian genes (globin, RSV, SV40, EMC, elastase, albumin, a-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding pVIP receptor. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO $DHFR^-$ cells (ATCC CRL-9096) and mouse $LTK^-$ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., (1982) *J. Molec. Appl. Genet.,* 1:327, mycophenolic acid, Mulligan, R. C. and Berg, P. (1980) *Science,* 209:1422 or hygromycin, Sugden, B. et al., (1985) *Mol Cell. Biol.,* 5:410–413. The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression of the pVIP receptor is pRc/CMV. A restriction site and function map of pRc/CMV appears in FIG. 3 of the accompanying drawings. pRc/CMV is commercially available from Invitrogen Corporation, 3985 Sorrento Valley Blvd., San Diego, Calif. A 92121.

To confirm correct sequences in plasmids constructed, the ligation mixtures are used to transform *E. coli* K12 strain DH5α (ATCC 31446) and successful transformants selected by antibiotic resistance where appropriate. Plasmids from the transformants are prepared, analyzed by restriction and/or sequence by the method of Messing, et al., (1981) Nucleic Acids Res. 9:309.

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al. (1989) *Molecular Cloning: A Laboratory Manual*, Cold Spring Harbor Press, Cold Spring Harbor Laboratory, Cold Spring Harbor, New York or *Current Protocols in Molecular Biology* (1989) and supplements.

Preferred suitable host cells for expressing the vectors of this invention encoding pVIP receptor in higher eukaryotes include: African green monkey kidney cell line transformed by SV40 (COS-7, ATCC CRL-1651); transformed human primary embryonal kidney cell line 293, (Graham, F. L. et al. (1977) *J. Gen Virol.*, 36:59–72, *Virology,* 77:319–329, *Virology,* 86:10–21); baby hamster kidney cells (BHK-21(C-13), ATCC CCL-10, *Virology,* (1962) 16:147); chinese hamster ovary cells CHO-DHFR⁻ (ATCC CRL-9096), mouse Sertoli cells (TM4, ATCC CRL-1715, *Biol. Reprod.,* (1980) 23:243–250); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065);and mouse mammary tumor cells (MMT 060562, ATCC CCL51).

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (ATCC-40053, Stinchcomb, et al., (1979) Nature 282:39; Kingsman et al., [1979] Gene 7:141; Tschemper et al., [1980] Gene, 10:157) is commonly used. This plasmid already contains the trp gene which provides a selection marker for a mutant strain of yeast lacking the ability to grow in tryptophan, for example ATCC no. 44076 or PEP4-1 (Jones, [1977], *Genetics,* 85:12).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from Saccharomyces cerevisiae (found in conjunction with the CYC1 promoter on plasmid YEpsec-hI1beta ATCC 67024), also are advantageously used with yeast promoters.

Prokaryotes also are used for expression. The aforementioned strains, as well as *E. coli* W3110 (prototrophic, ATCC No. 27325), bacilli such as Bacillus subtilis, and other enterobacteriaceae such as Salmonella typhimurium or Serratia marcescans, and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., [1978] *Nature,* 275:615; and Goeddel et al., [1979] *Nature,* 281:544), alkaline phosphatase, the tryptophan (trp) promoter system (vector pATHi [ATCC 37695] is designed to faciliatate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding pVIP receptor using linkers or adapters to supply any required restriction sites. Promoters for use in bacterial systems also will contain a Shine-Dalgarno sequence operably linked to the DNA encoding pVIP receptor.

PVIP receptor includes amino acid sequence mutants, glycosylation variants and covalent or aggregative conjugates with other chemical moieties. These pVIP receptor, functional derivatives, as well as glycosylation variants and covalent or aggregative conjugates with other chemical moieties may be used according to conventional techniques for the construction and isolation of antibodies against these molecules. See e.g., Kohler and Milstein (1975) *Nature,* 256:497. PVIP receptor include covalent derivatives prepared by linkage of functionalities to groups which are found in the pVIP receptor amino acid side chains or at the N, or C-termini, by means known in the art. These derivatives may, for example, include: aliphatic esters or amides of the carboxyl terminus or residues containing carboxyl side chains, O-acyl derivatives of hydroxyl group-containing residues, and N-acyl derivatives of the amino terminal amino acid or amino-group containing residues, e.g. Lysine or arginine. Acyl groups are selected from the group of alkyl-moieties (including C3 to C18 normal alkyl), thereby forming alkaloyl aroyl species.

A major group of derivatives are covalent conjugates of pVIP receptor or their fragments with other proteins or polypeptides. These derivatives are synthesized in recombinant culture as N, or C-terminal fusions or by the use of bifunctional agents known per se for use in cross-linking proteins to insoluble matrices through reactive side-groups. Preferred pVIP receptor derivatization sites with cross-linking agents are at cysteine and lysine residues. Preferred agents are N-maleimidobenzoyl succinimide ester and N-hydroxysuccinimide.

Covalent or aggregative derivatives are useful as immunogens, reagents in immunoassay or for affinity purification procedures of pVIP or other binding ligands. For example, pVIP receptor is insolubilized by covalent bonding to cyanogen bromide-activated Sepharose by methods known per se or adsorbed to polyolefin surfaces (with or without glutaraldehyde cross-linking) for use in the assay or purification of anti-pVIP receptor antibodies or pVIP. pVIP receptor also is labeled with a detectable group, e.g., radioiodinated by the chloramine T procedure, covalently bound to rare earth chelates or conjugated to another fluorescent moiety for use in diagnostic assays.

The ability of pVIP to bind to the pVIP receptor is essential in the vasodilative effects of VIP on target tissues., It therefore would be desirable to determine those agents which interfere with the formation of the [VIP/pVIP receptor] complex. The instant invention provides such a screening system useful for discovering agents which compete with VIP for binding to the pVIP receptor, said screening system comprising the steps of:

a) recombinantly producing a pVIP receptor, b) exposing said pVIP receptor to a potential inhibitor of the [VIP-pVIP receptor] complex, c) introducing VIP, d) removing non-specifically bound molecules, and e) quantifying the concentration of bound potential inhibitor and/or VIP.

This allows one to rapidly screen for inhibitors of the formation of the [VIP/pVIP receptor] complex. Utilization of the screening system described above provides a sensitive and rapid means to determine compounds which interfere with the formation of the [VIP/VIP receptor] complex. This screening system may also be adapted to automated procedures such as a Pandex® (Baxter-Dade Diagnostics) system allowing for efficient high-volume screening for potential therapeutic agents.

The procedure of such a screening protocol proceeds as follows. A pVIP receptor is prepared as elsewhere described herein, preferably using recombinant DNA technology. A sample of a test compound is then introduced to the reaction vessel containing the pVIP receptor followed by the addition of VIP. Unbound molecules are washed free and the eluent inspected for the presence of VIP or the test compound.

For example, in a preferred method of the invention, radioactively or fluorescently labeled VIP may be used. The eluent is then scored for fluorescence or radioactivity. The absence or diminution of fluorescence or radioactivity indicates the formation of the VIP/pVIP receptor complex. This indicates that the test compound has not disrupted the formation of the VIP/pVIP receptor complex. The presence of fluorescence or radioactivity indicates that the test compound has disrupted the formation of the VIP/pVIP receptor complex. Similarly, a radioactively or fluorescently labeled test compound may be used in which case the same steps as outlined above would be used except that the interpretation of results would be the converse of using radioactively or fluorescently labeled VIP.

The DVIP receptor may be free in solution or bound to a solid support. In the preferred practice of the invention, the DVIP receptor is bound to a solid support. Examples of such solid supports include insoluble natural or synthetic polymers, such as a porous membrane, bead, microparticle, chromatographic resin, microtiter plate, mica, and the like. A variety of cross-linking methods, such as through the side chains of lysine residues or other various chemical means, are well known in the art and may be used for immobilizing the pVIP receptor to a solid supports.

The previously described screening system identifies compounds which competitively bind to the pVIP receptor. Determination of the ability of such compounds to stimulate or inhibit the action of the pVIP receptor is essential to further development of such compounds for therapeutic applications. The need for an bioactivity assay system which determines the response of the pVIP receptor to a compound is clear. The instant invention provides such a bioactivity assay, said assay comprising the steps of:

a) transfecting a mammalian host cell with an expression vector comprising a DNA encoding a pVIP receptor and a signal peptide, b) culturing said host cell under conditions such that the DNA encoding the pVIP receptor and signal peptide are expressed, c) exposing said host cell so transfected to a test compound, and d) quantifying the intracellular cAMP level in response to said test compound.

In the preferred practice of the invention as exemplified herein, a stable 293 cell line containing the pRC/CMV-VIPR (as prepared in accordance with the Examples herein) was grown to confluency in 24-well plates. The cells were then incubated at 37° C. for approximately 45 min in a solution containing various concentrations of test compounds ($10^{-5}$ to $10^{-11}$M). After removing the solution, 0.5 ml of 60% ethanol was added to lyse the cells in each well. An aliquot was taken, dried in vacUo, and the level of cAMP was determined. Intracellular cAMP levels were determined using the procedure described by Ishihara et al., (1991) using a cyclic AMP assay kit (Cat. no. TRK.432), commercially available from Amersham Corporation 2636 South Clearbrook Drive, Arlington Heights, Ill. 60005.

EXAMPLES

The following examples are provided to further illustrate the invention described herein but are not intended to be limitations thereof.

EXAMPLE 1

ISOLATION OF TOTAL RNA FROM PORCINE PITUITARY AND LUNG TISSUES

The following procedure was adapted from the procedure as disclosed in Sambrook, J., Fritch, E. F., and Maniatis, T. (1989) Molecular Cloning, vol 1, p. 7.19–7.22. Briefly, 25 ml of 4M Guanidine isothiocyanate buffer [16.7 mM sodium citrate, 0.5% sodium lauryl sarcosine, 0.17% antifoam A and 0.7% beta-mercaptoethanol, pH 7.0] were added to 3.5 g of pig pituitary OR lung (commercially available from Pel-Freez Inc., AR) in a 50 ml sterile Falcon tube. The tissue was homogenized with a tissuemizer at high speed for 1–2 min. The homogenized tissue was centrifuged at 5000×g for 5 min at room temperature.

The supernatant was layered onto a 9.5 ml cushion of 5.7M CsCl, 16.6 mM sodium acetate in a Beckman centrifuge tube for SW28 rotor. The material was centrifuged at 25° C. for 24 hrs at 25,000 rpm. After removing supernatant, drain out liquid and cut off the bottom of the tube. The pellet was rinsed with 70% ethanol at room temperature and dried at room temperature.

The pellet of RNA was redissolved in sterile Milli-Q® water. The RNA was purified by phenol extraction, and then precipitated by the addition of ethanol. The pellet was rinsed with 70% ethanol and dried in vacuo. Approximately 4.9 mg of total RNA was isolated from 3.5 g of pig lung tissues.

EXAMPLE 2

CDNA Synthesis From Total RNA

The following procedure was performed using a BRL kit (Catalog No. 80255A/SB) in substantial accordance with the instructions provided by the manufacturer. Briefly, porcine lung total RNA (1 mg/ml, 1 μl prepared in accordance with Example 1 above) was mixed with 1 μl of 50 μM random hexamer primer (commercially available from Perkin Elmer-Cetus as part of the GeneAmp® PCR Kit No.N808–0017) and 10 μl Milli-Q® water in a 1.5 ml Eppendorf tube. The mixture was heated to 70° C. for 10 min, chilled on ice for 2 min , and spun down in a microcentrifuge for one second. Four μl of 5× reaction buffer (250 mM Tris-HCl, pH 8.3,375 mM KCl, 15 mM MgCl$_2$), 2 μl of 0.1M DTT, 1 μl of dNTP stock (10 mM each of dATP, dGTP, dCTP, and dTTP at pH 7.0) was then added to the sample and the mixture was incubated at 37° C. for 2 min. One μl of M-MLV-reverse transcriptase (200 U/μl , BRL) was added and the reaction mixture was incubated at 37° C.

for 1 hour. The mixture was heated at 95° C. for 5 minutes, cooled on ice for 5 minutes and spun for 1 second. This random primed cDNA reaction mixture was then used for PCR amplification in accordance with the teaching of Example 3 below.

EXAMPLE 3

PCR AmplifiCation

The following procedure was performed using a Perkin Elmer-Cetus Gene Amp PCR Reagent Kit (commercially available from The Perkin Elmer-Cetus Corporation, 761 Main Avenue, Norwalk CT 06859-0156) in substantial accordance with the teaching of the instructions provided therewith. Briefly, in a sterile 0.5 ml tube, add 10 µl of a 10× reaction buffer, 16 µl of dNTP mixture (each at 1.25 mM), 25 pmoles of up-stream primers 25 pmoles of down-stream primer, 1 µl of the cDNA reaction mixture or 1 µl of 1:10 dilution of the cDNA reaction mixture. Sterile Milli-Q® water was added to achieve a final volume of 99 µl. One µl of diluted (1:2 or 1:3) AmpliTAQ DNA polymerase (5 U/µl, commercially available from Perkin Elmer-Cetus) then added. The reaction mixture was mixed and one drop (about 50 µl) of mineral oil (commercially available from Sigma Chemical Co.) was added. PCR was carried out for 30 cycles in 3 steps:

(a) denaturation step, 30 seconds at 95° C.;
(b) annealing step, 1 min at 5° C.–10° C. below $T_m$ of primers;
(c) polymerization step, 1 min at 72° C. 10 µl of the PCR reaction mixture was withdrawn after reaction was completed and electrophoresed on a 6% acrylamide gel or 0.7% agarose gel for analysis. The analyzed PCR products showed the following oligonucleotide pairs gave a 700bp cDNA fragment.

Degenerate oligonucleotide primers:

downstream primer (Sequence ID#3) 5'-CTGCACCT-CACCATTGAGGAAGCAGTA-3'
upstream primer (Sequence ID#4) 5'-TTCCGGAGGCT-GCAYTGCACYCGMAACTACAT 3'
wherein Y=C or T and M=A or C

EXAMPLE 4

Cloning of PCR Products

EXAMPLE 4.a

Amplification of the 700 bp Fragment by PCR

The aforementioned 700 bp cDNA fragment was purified on 6% polyacrylamide gel as above. The approximately 700 base pairs gel band was excised and soaked in sterile Milli-Q® water (approximately 500 µl) for approximately 5 hours or overnight at room temperature. Using 3 µl of soaking solution as a template, the same (3 and 4) oligonucleotides as primers, another PCR amplification was run under the same PCR conditions as described above. The second PCR products were electrophoresed on a 6% polyacrylamide gel. DNA bands corresponding to approximately 700 base pairs were excised from the gel. The DNA was electroeluted from the gels (1× TBE, 50 volts/overnight using equipment commercially available from Epigene). After precipitation of DNA, the DNA pellet was resuspended in 50 µl of Milli-Q® water.

EXAMPLE 4.b

Prepare blunt-end DNA fragments

5 µl of 10× Kinase buffer (500 mM tris-HCl, pH 7.5, 100 mMMgCl$_2$, 100 mM DTT), 5 µl of 10 mM ATP, 5 µl of 2.5 mM dNTPs, 10 µl of T4 DNA polymerase (1U/µl, commercially available from Pharmacia), 1 µl of T4 DNA kinase (10 U/µl, Pharmacia) and 4 µl of sterile water and of the purified cDNA fragment (700 bp) were combined in a 1.5 ml Eppendorf tube. The reaction mixture was incubated at 37° C. for 1 hour. The enzymes were then inactivated by incubation at 68° C. for 10 min.

EXAMPLE 4.c

Ligation; Transformation pUC18 DNA (0.1 micrograms linearized with SmaI) was ligated to blunt-ended PCR fragments (0.06 µg, 700 basepairs) in the presence of 3 µl of 10× Kinase buffer, 1.5 µl of 10 mM ATP, 3 µl of sterile water and 1 µl of T4 DNA Ligase (BRL) at 14° C. overnight in a final volume of 20 µl. The ligation mixture was diluted with TE buffer (pH 7.4) to 1:5. 5 µl of the diluted ligation mixture was used to transform 80 µl DH5µl competent cells (commercially available from BRL).

After incubation on ice for one hour, the cells were heat shocked at 42° C. for 45 seconds and then chilled on ice for 10 min. 800 µl S.O.C. medium (commercially available from BRL) was added and the reaction mixture was incubated for another 1 hour at 37° C. Cells were plated on TY agar containing 0.4% Xgal, 50 µM IPTG and 100 µg/ml ampicillin (Ap) and then incubated at 37° C. overnight.

EXAMPLE 4.d

Screen Transformants by PCR 12 white colonies from the plates were picked and used to inoculate 3 ml TY medium containing 100 µg/ml Ap and cultured at 37° C. for 4 hours. 5 microliters of culture was added to a solution containing 5 µl of 10× PCR buffer, 8 µl of 1.25 mM dNTPs, 0.5 µl of 1% gelatin, 0.5 µl of 10% Triton x-100, 1 µl of 15 µM universal forward primer No. 2977 ($T_m$=50° C.) having DNA sequence:

5'-GTAAAACGACGGCCAGT-3' (Sequence ID#5) 1 µl of 15 µM universal reverse primer (No. 2976, $T_m$=50° C.) having DNA sequence:
5'-CAGGAAACAGCTATGAC-3'(Sequence ID#6) and 28 µl of sterile water. The mixture was heated to 95° C. for 15 min and quickly cooled on ice. One µl of TAQ DNA polymerase (2.5 U/µl) (commercially available from Perkin Elmer Cetus) and 50 µl of mineral oil was added to the reaction mixture. PCR was run for 30 cycles: 95° C., ½ min.; 40° C., 1 min.; 72° C., 1 min.

A 10 µl sample of the resulting reaction mixture was electrophoresed on a 6% polyacrylamide gel. The colonies producing a band of about 700 bp size were selected as candidates and were subjected to sequencing analysis.

EXAMPLE 5

Preparation of 32P-DNA Probe Using PCR

PCR was used to prepare 700 bp cDNA hybridization probes to screen porcine lung cDNA library to isolate the pVIP receptor cDNA, The [32P]-cDNA probes were prepared in the following manner. The reaction mixture containing 4 μl of 10×PCR buffer, 3 μl of a mixture of dATP, dGTP and dTTP (0.2 mM each), 2 μl of template plasmid DNA (5 nanograms/microliter), 40 picomoles of each primer, 20 μl [32P]-α-dCTP (3000Ci/mmole), 1 microliter of TAQ DNA polymerase (5 U/μl) and sterile water was added to adjust the total volume to 40 μl. After PCR amplification was done, purified [$^{32}$P]-DNA probe was isolated using a Quick-spin column (G-50 Sephadex®, commercially available from Boehringer Mannheim) to eliminate free [32P]-α-dCTP.

EXAMPLE 6

Isolation of POLY-A+ RNA

Porcine lung total RNA was isolated in substantial accordance with the teaching of Example 1 above. Polyadenylated mRNA was isolated using a Quick Prep™ mRNA Purification Kit (commercially available from Pharmacia, Piscataway, N.J.) in substantial accordance with Procedures A and B of the instructions provided by the manufacturer. The resulting precipitate RNA was redissolved in an 25 μl volume of sterile water.

For RNA, one A260 absorbance unit=40 μg/ml, the concentration of RNA present in the elute was calculated using the following formula:

$$[RNA] = A_{260} \times D \times 40 \text{ μg/ml}$$

where D=final dilution factor. A260 for the elute was found to be 0.4578 with a dilution factor of 100 indicating a RNA concentration of 1831 μg/ml, or approximately 1.8 μg/μl

EXAMPLE 7 cDNA SyntheSis end LAMBDA Cloning

The Superscript™ Lambda System (commercially available from GIBCO-BRL, Gaithersburg MD) was used for cDNA Synthesis and. Cloning of the using isolated poly A+ RNAo 10 μg of Poly A+ RNA was used for cDNA synthesis. The cDNA synthesis was performed in substantial accordance with the protocol described in GIBCO-BRL instructions for the SuperScript™ Lambda System. The packaging of cDNA was performed using the λ Packaging System (commercially available from GIBCO-BRL, Gaithersburg MD as catalog No. 8294SA) in substantial accordance with the instructions provided by the vendor.

EXAMPLE 8 screen CDNA Library

Mix 100 μl packaged cDNA-containing phage to 4 ml of cultured Y1090 (r−) cells. Two-hundred B1 from infected Y1090 (r−) cells was added to 8 ml soft TY agar containing 10 mM MgCl$_2$ and overlayed on a 150 mm plate with TY agar and incubated overnight at 37° C. Twenty plates (or approximately 1,000,000 phage) were screened. The plates were refrigerated for 2 hours at 4° C. before lifting with Hybond-N® nylon membranes to prevent top agar from sticking to the membranes. The phage were transferred for 2 minutes onto Hybond-N® membranes before lifting and marked through the agar for orientation. When making duplicates, the 2nd filter was allowed to transfer for approximately 7 minutes.

The filters were denatured after lifting by submerging in denaturing solution (1.5M NaCl, 0.5M NaOH) for 2 minutes. The filters were neutralized for 5 minutes by submerging in neutralising solution (1.5M NaCl, 0.5M Tris-Cl pH 8.0). The filters were rinsed for approximately 30 seconds only, and then submerged in (0.2M Tris-Cl pH 7.5, 2×SSC). The filters were allowed to air dry on Whatman 3MM paper and baked at 80° under vacuum for two hours.

EXAMPLE 9

Filter Hybridization

Filter hybridization was performed in substantial accordance with the teaching of Hamilton, et al., Nucleic Acids Research 19:1951–1952 (1991). Briefly, 40 filters are placed in a Seal-a-Meal® bag to which is added 100 ml of the hybridization buffer (50% formamide, 5×SSPE, 1× Denhardts solution, 1% SDS, 100 mg/ml salmon sperm DNA) followed by prehybridization at 42° C. for 1 hour. Add 100 μl of the PCR-generated $^{32}$P-probe as described in Example 5 above (total radioactivity 1×10$^9$ cpm) to prehybridized filters then hybridize at 42° C. overnight. Wash filters 3 times at ambient temperature with 0.1×SSPE/0.13% SDS with shaking 20 minutes/wash. Repeat wash 3 times at 47° C. with 0.1×SSPE/0.3% SDS with shaking 20 minutes/wash. Mount filter on plastic film and autoradiograph with intensifying screen at −80° C. overnight.

EXAMPLE 10

Making a Liquid Lysate

Host bacteria (Y1090(r−)) were grown to stationary phase overnight and infected with 10$^5$ to 10$^8$ phage/ml. Following phage adsorption, the infected E. coli culture was diluted into a rich medium and shaken vigorously until cell lysis. Any remaining viable cells were lysed with chloroform. Cell debris was removed by low-speed centrifugation.

An overnight culture of a lambda-sensitive strain of E. coli was grown in LB medium at 37° C. Lambda-sensitive strains will support lytic growth. This can be tested by spotting 10 μl of lambda lysate onto a lawn of bacteria. If the strain is lambda-sensitive, a plaque will form where the phage were spotted. Using a sterile toothpick or capillary tube, a single plaque was picked and blown into a tube that contains 0.4 ml lambda dilution buffer and placed at 4° C. for 2 hr to allow phage to elute. Alternatively, 10$^5$ to 10$^8$ phage from a liquid lysate or plate stock can be used.

One-hundred μl eluted phage was combined with 100 μl of saturated culture and 100 μl of 10 mM MgCl$_2$/10 mM CaCl$_2$ solution and incubated 15 min in a 37° C. water bath. Incubation with Mg$^{++}$ and Ca$^{++}$ allowed the phage to adsorb to the bacteria. This solution was transferred to 50 ml of NZC medium and shaken vigorously at 37° C. until lysis occurred (approximately 6 and 8 hr). Good aeration is important for high yields. The culture should be checked frequently after 6 hr, and harvested immediately upon clearing.

Add a few drops of chloroform to lyse any remaining cells, the solution was carefully transferred to Corex® or Nalgene® centrifuge tubes (being careful to leave the chloroform behind), and spun 10 min at 10,000 rpm in a Beckman JA-20 rotor to pellet the cell debris. Save as much of the lysate as desired. The solution was transferred to a screw-cap tube, to which a few drops of chloroform were added and the solution briefly vortexed and stored at 4° C.

The titer of the phage should be determined as described in *Current Protocols in Molecular Biology*, and Supplements, Ausubel, et al Eds.,(1989 and supplements) John Wiley and Sons, New York Unit 1.11.

EXAMPLE 11

Isolate PHAGE DNA and Clone cDNA into Plasmid pSPORT1

The following protocol was used for making small quantities of DNA to be used for restriction analysis. Phage were concentrated by centrifugation and their capsids were destroyed with phenol. The DNA was then ethanol precipitated.

The following additional materials were used in this and following examples:

5 mg/ml DNase (as described in *Current Protocols in Molecular Biology*, and Supplements, Ausubel, et al Eds.,(1989 and supplements) John Wiley and Sons, New York Unit 3.12)

10 mg/ml DNase-free RNase (as described in *Current Protocols in Molecular Biology*, Supra Unit 3.13)

0.05M Tris-Cl, pH 8.0

3M sodium acetate, to pH 4.8 with acetic acid

To approximately 50 ml liquid phage lysate (*Current Procols in Molecular Biology*, supra Unit 1.12), 10 ml of 5 mg/ml DNase and 25 ml of 10 mg/ml DNase-free RNase were added and the reaction mixture was incubated for 1 hr at 37° C. to degrade the bacterial DNA and RNA released during lysis. The viscosity of the mixture should decrease. The reaction mixture was centrifuged for 1½ hr at 27,000 rpm in an SW-28 rotor (132,000×g), 4° C. Alternatively, the phage may be pelleted by spinning 2¼ hr in JA-20 rotor at 20,000 rpm (48,000×g), 4° C.

Resuspend the phage pellet in 200 μl of 0.05M Tris-Cl, pH 8.0. A small translucent pellet was visible after the tubes are inverted. Transfer the solution to a microcentrifuge tube and add 200 μl buffered phenol and vortex for 20 min or shake for 20 min in microcentrifuge tube shaker. The tube was spun for 2 min in microcentrifuge and the aqueous (top) layer was saved. Phenol extraction was repeated. Phenol denatures the phage capsids and releases the DNA. This denatured capsid protein appeared as a thick white precipitate at the phenol/water interface. Vigorous agitation was necessary to resuspend the pellet. There should be less white precipitate after the second phenol extraction. If there is still a large amount at the interface, do a third extraction.

200 μl chloroform was added, the mixture shaken well, and spun briefly in a microcentrifuge. The aqueous (top) layer was saved and the process repeated. 20 μl of 3M sodium acetate, pH 4.8, was added and the DNA precipitated with 2 vol of 100% ethanol at room temperature. The mixture was spun in microcentrifuge for 10 min and the supernatant discarded. The pellet was washed with 1 ml of 70% ethanol. The pellet was dried under a vacuum and the DNA resuspended in 25 μl TE buffer, pH 8.0.

The phage DNA was resuspended in 25 μl TE buffer, 5 μl 1 10× high salt buffer (Boehringer-Mannheim), 16 μl H$_2$O, NotI 2 μl (10 U/μl Boehringer-Mannheim) and SaiI 2 μl (10 U/μl Boehringer-Mannheim). The digestion mixture was incubated at 37° C. for 2 hours. 50 μl of the digestion mixture was run on a 1% low melting agarose gel. A 2.7 kb cDNA fragment was excised and melted at 65° C. This cDNA fragment was then ligated to a linearized plasmid pSPORT1 in accordance with the following procedure.

Plasmid pSPORT 1 is a multifunctional expression vector for oriented cDNA cloning, in vitro transcription, and dideoxy sequencing. This vector is commercially available from Gibco BRL, Gaithersburg MD. To the 20 μl (1 μg) of NotI-SalI linearized pSPORT 1 was added 30 μl of the 1.6 kb cDNA fragment, 6 μl 10× kinase buffer, 3 μl 10 mM ATP pH 7.0 & 2 μl T4 DNA Ligase 1μ/μl BRL). The mixture was incubated overnight at 14° C.

The ligation mixture was melted for 10 minutes at 65° C. 50 μl of melted ligation mixture was added to 200 μl competent DH5α cells on ice and incubated on ice for 30 minutes. One ml of TY broth was added and incubated at 37° C. with shaking for 1 hour. The transformed cells in TY broth were plated on TY-Ap(100 μg/ml Ap) agar and incubated overnight at 37° C.

EXAMPLE 12

Large Scale Plasmid Preparation

Three colonies from the plates prepared in Example 11 were picked and used to prepare large quantities of the plasmid pSPORT1 containing the cDNA fragment. The large scale plasmid was prepared in substantial accordance with the teaching of Sambrook, J., Fritsch, E. F., and Maniatis, T., 1989. *Molecular Cloning: A Laboratory Manual*, Cold Spring Harbor (1989). Sequence analysis of the cDNA fragment cloned into the plasmid pSPORT1 showed that the cDNA encoded a purtative pVIP receptor of 451 amino acids. This plasmid was designated as pSPORT-VIPR

EXAMPLE 13

Cloning of VIPR cDNA Fragment into pRC/CMV Vector

EXAMPLE 13.a

Digestion of plasmid PRC/CMIr by Hind III and Not I

22 μl (26 micrograms) of plasmid PRC/CMV (Invitrogen) were digested by 5 μl of Hind III (10U/μl) in 3 μl of 10×M buffer (Boehringer Mannheim) at 37° C. for 1.5 hours. Then add 1.3 μl of 1M Tris-HCl (pH 7.5), 1 μl of 1.5M NaCl, 0.5 μl of 10×M buffer and 5 μl of NotI (10U/microliter). Incubate the mixture at 37° C. for 1.5 hours. Run the 0.7% agarose gel electrophoresis with the reaction mixture and one band (5.4 Kb) was observed. Cut the 5.4 Kb band and purify the vector DNA using Spin-Bind DNA Extraction Units (FMC)

EXAMPLE 13.b

Preparation of VIPR cDNA fragments

5 μg of the starting plasmid, pSPORT-VIPR (for pVIP receptor cDNA) was digested by 10 units of SalI enzyme and 10 units of NotI enzyme in a 40 μl SalI buffer at 37° C. for 2 hours. The enzymes were inactivated by heating to 70° C. for 10 min. The 2.7 kb fragment was purified on 0.7 % agarose gel and 2.7 kb fragment was excised and purified by using Spin Bind DNA extraction units (FMC Corporation)

EXAMPLE 13.c

Ligation and transformation

The NotI-HindIII linearized pRC/CMV vector DNA (Example 13.a.), 2.7 kb NotI/SalI cDNA fragment (Example 13.b.) and SalI/HindIII linker (5'-AGCTTACCGGTG-3' Seq. ID.#7 and 5'-TCGACACCGGTA-3' Seq. ID.#8) were ligated in the presence 1× Kinase buffer, 0.5 mM ATP and 1U T4 DNA ligase (Gibco-BRL) at 16° C. overnight. The ligation mixture was then transformed into DH5α competent cells (BRL).

EXAMPLE 14

CHARACTERIZATION OF pRC/C.MV-VIPR

EXAMPLE 14.a

Digestion pRC/CMV-VIPR contains unique SalI and NotI sites and the vector was subjected to digestion using SalI/NotI enzymes (Boehringer-Mannheim). PRC/CMV-VIPR candidates produced the 5.4 Kb fragment of vector DNA and the 2.7 Kb fragment of insert DNA.

EXAMPLE 14.b

Sequencing the Boundary Regions Between Insert and vector

The universal primer of pRC/CMV vector plasmid was used to sequence the boundary region between the insert and the vector (USB sequenase version 2.0 DNA sequencing kit) of two pRC/CMV-VIPR candidates. Sequencing data indicated that these two pRC/CMV-VIPR have correct pVIP receptor sequences.

EXAMPLE 15

Transfection of 293 Cells With PRC/CMV-VIPR

Trypsinize exponentially growing 293 cells, inoculate 10 cm plate with 293 cells at $2\times10^6$ cells/plate and incubate plates at 37° C./5% $CO_2$ for overnight in 10 ml EF 10 medium per plate.

Plasmids pRC/CMV-VIPR and pRC/CMV are used in transfection. Dilute 20 μg of DNA with sterile Milli-Q water to 450 μl. Add 50 μl of 2.5M $CaCl_2$, 500 μl of 2× BBS buffer [N, N-bis (2-hydroxyethyl)2-amino-ethanesulfonic acid and buffered saline, pH 6.95), and mix gently. Incubate the mixture at room temperature for 20 min. Gently mix the milky precipitate, and slowly add 1 ml of the milky DNA suspension into the culture, swirl the plate gently to distribute the DNA precipitate evenly. Incubate the plates at 37° C./5% $CO_2$ for 42 hrs.

EXAMPLE 16

Isolation of Total RNA from Transfected 293 Cells

Total RNA from transfected 293 cells was isolated using the RNA Isolation Kit from Promega in substantial accordance with the Promega Technical Bulletin included therewith. Use three plates of cells to isolate total RNA. Remove cell culture media. Wash cells with ice chilled sterile PBS buffer. Use 8 ml of prechilled denaturing solution (25 grams of guanadinium thiocynate dissolved in 33 ml of CBS [citrate/sarcosine/β-mercaptoethanol] buffer) to lyse 3 plates of cells. Transfer the cell lysate into a 50 ml plastic centrifuge tube. To the cell culture was added 0.8 ml of 2M NaOAc (pH 4.0), mixed well by inversion. Eight ml of phenol:chloroform:isomyl alcohol, was then added and the suspension mixed by inversion, vortexed for 10 seconds and then chilled on ice for fifteen minutes. The suspension was centrifuged (7000 rpm) at 4° C. for 20 min. The top aqueous phase which containing the RNA was transferred into a new 50 ml tube. An equal volume of isopropanol was added to the RNA solution. The RNA was pelleted after it precipitated at −20° C. overnight. The pellet was washed with ice cold 75% ethanol, dried in vacuo and dissolved in 100 μl of sterile water.

EXAMPLE 17

Northern Blot Analysis

Prepare a 1.1% agarose gel which contains 17% formaldehyde and 1× MOPS. The RNA sample contains 25 μg total RNA, 50% formamide, 17% formaldehyde, 1× MOPS, 1× dye and 1 μg Ethidium bromide (EtBr). Heat the sample at 65° C. for 15 min. Cool on ice for 2 min. Run RNA gel in 1× MOPS buffer at 100 voltage for 3 hrs. After taking a photo of the gel under UV, rinse the gel with distilled water once. Soak the gel in 20×SSC at room temperature for 10 min twice. Transfer the denatured RNA to nylon membrane (Hybond-N) overnight. After blotting, mark the position of the gel slots on the filter. Soak the filter in 6×SSC at room temperature for 5 min. The RNA was fixed on nylon membrane using a Stratalinker® UV Crosslinker (commercially available from Stratagene, 11099 North Torrey Pines Road, LaJolla Calif. 92037), the filter was air dried and placed in a plastic bag to which was added a 15 ml of hybridization buffer [1 mM EDTA, 0.5M $NaH_2PO_4$, pH 7.2, 7% SDS] and prehybridized at 65° C. for 2 hrs with shaking. The solution was removed and another 15 ml of hybridization buffer and $[^{32P}]$-DNA probe (PCR) at $1-2\times10^8$ cpm, hybridized at 65° C. with shaking overnight. The filter was washed in 200 ml of solution containing 1 mM EDTA, 40 mM $NaH_2 PO_4$ (pH 7.2), 1% SDS at 65° C. for 1 hour twice. Expose the filter to x-ray film (Kodak XAR 5) at room temperature or −70 C. with an intensifying screen for an adequate time.

EXAMPLE 18 pVIP Receptor Expression in Stably Transfected 293 cells

The vector pRC/CMV-VIPR was transfected into 293 cells by calcium phosphate co-precipitation procedure (Example 17). Cells were allowed to grow for 3–4 days before adding Geneticin (G-418) to the media at a concentration of 300 μg/ml for the selection of permanently transfected clones. After 2–3 weeks, 24 clones were selected for analysis of intracellular cAMP accumulation. The clone (293/VIPR) that gave the highest accumulation of cAMP in response to VIP challenge was established and used to study the function and binding characteristics of the cloned receptor.

EXAMPLE 19 cAMP Assay

The intracellular cAMP levels were assayed following essentially the procedure decribed by Ishihara et al., (1991) using a cyclic AMP assay kit (Cat. no. TRK.432), commercially available from Amersham Corporation 2636 South Clearbrook Drive, Arlington Heights, Ill. 60005. In brief, the stable 293 cell line containing the pRC/CMVVIPR was grown to confluency in 24-well plates coated with poly-D-lysine. Cells were washed twice with the incubation buffer (Dulbecco's modified Eagle's medium containing 0.5 mM 1-methyl-3-isobutylxanthine and 1 mg/ml BSA). The cells were then incubated at 37° C. for 45 min in the buffer (0.5 ml) containing various concentrations of peptides ($10^{-6}$ to $10^{-11}$M). After removing the buffer, 0.5 ml of 60% ethanol was added to lyse the cells in each well. An aliquot (10 μl) was taken to be dried in vacuo and the level of cAMP was determined using the Cyclic AMP Assay Kit (Amersham, catalog No. TRK 432).

EXAMPLE 20

Binding of $^{125}$-VIP TO 293/vipr Cells

Binding assays were performed on a monolayer 293/vipr culture grown in 48-well plates. The wells were precoated with poly-D-lysine in order to increase cell attachment to the surface. The 293/vipr cells expressing the pVIP receptor were allowed to grow to confluency in the culture medium EFP10 containing 300 μg/ml Geneticin (G418). The confluent cells (approximately $10^5$ cells/well) were then washed twice with cold receptor assay buffer (Hepes-buffered saline containing 0.1% protease-free BSA). The radioreceptor assay was then performed in triplicate by using 0.125 nM of $[^{125}I]$-VIP in the incubation buffer and each of three unlabeled hormone competitors (VIP, GHRH and secretin) at various concentrations ($10^{-5}$ to $10^{-11}$M). The incubation was performed for 45–60 minutes at 37° C. and the cells washed three times with Hank's Balanced Salt solution. $[^{125}I]$-VIP bound to the cells was then determined in a gamma counter after the cells were lysed with 0.5 ml of 0.5N NaOH in each well.

---

We claim:

1. An isolated pVIP Receptor comprising the amino acid sequence which is Sequence ID#2.

2. An isolated DNA encoding the pVIP Receptor of Sequence ID#2.

3. The DNA of claim 2 comprising the DNA sequence which is Sequence ID#1.

4. A recombinant DNA vector comprising the DNA of claim 2.

5. The recombinant DNA vector of claim 4 wherein said vector comprises the DNA sequence which is Sequence ID#1.

6. A recombinant host cell transformed with the vector of claim 4.

7. The recombinant host cell of claim 6 wherein the vector comprises the DNA sequence which is Sequence ID#1.

8. A method of producing a pVIP protein comprising the steps of:

a) placing the DNA of claim 4 into an expression vector in a manner suitable for the expression of the pVIP Receptor either alone or as a fusion protein, b) transforming an appropriate host cell with said expression vector, c) culturing said host cell under conditions to facilitate expression of said DNA, and d) recovering the recombinantly produced pVIP Receptor.

9. The method of claim 8 wherein said DNA comprises the DNA sequence which is Sequence ID#1.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1377 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1377

( x i ) SEQUENCE DESCRIPTION: SEQ ID NO:1:

```
ATG  CGC  CCC  CTG  AGC  CCG  CCG  CCG  GCC  GGC  TGG  TTC  TGC  GTG  CTG  GCC         48
Met  Arg  Pro  Leu  Ser  Pro  Pro  Pro  Ala  Gly  Trp  Phe  Cys  Val  Leu  Ala
 1                    5                        10                       15

GGC  GTC  CTC  GCC  TGT  GTC  CTC  GGC  CCC  GTG  GGC  AGC  TGG  GCA  GTC  GGG         96
Gly  Val  Leu  Ala  Cys  Val  Leu  Gly  Pro  Val  Gly  Ser  Trp  Ala  Val  Gly
                     20                        25                       30

TTG  CAG  CAG  GAG  GAG  TGT  GAC  TAT  CTG  CAG  ATG  ATC  AAG  GTA  CAG  CAC        144
Leu  Gln  Gln  Glu  Glu  Cys  Asp  Tyr  Leu  Gln  Met  Ile  Lys  Val  Gln  His
           35                        40                       45

AAG  CAG  TGC  CTG  GAG  GAA  GCC  CAG  CTG  GAG  AAT  GAA  ACA  TCA  GGC  TGC        192
Lys  Gln  Cys  Leu  Glu  Glu  Ala  Gln  Leu  Glu  Asn  Glu  Thr  Ser  Gly  Cys
     50                        55                       60

AGC  AAG  ATG  TGG  GAC  AAC  CTC  ACC  TGC  TGG  CCA  GCC  ACC  CCT  CGG  GGA        240
Ser  Lys  Met  Trp  Asp  Asn  Leu  Thr  Cys  Trp  Pro  Ala  Thr  Pro  Arg  Gly
65                        70                       75                       80

CAG  GTG  GTT  GTC  TTA  GCT  TGC  CCT  CTC  ATC  TTT  AAG  CTC  TTC  TCT  CCC        288
Gln  Val  Val  Val  Leu  Ala  Cys  Pro  Leu  Ile  Phe  Lys  Leu  Phe  Ser  Pro
                     85                        90                       95

ACT  CAA  GGC  CTC  AAC  GTG  AGC  CGC  AAC  TGC  ACA  GAC  GAG  GGC  TGG  ACG        336
Thr  Gln  Gly  Leu  Asn  Val  Ser  Arg  Asn  Cys  Thr  Asp  Glu  Gly  Trp  Thr
                    100                       105                      110

CCC  CTG  GAG  CCT  GGC  CCC  TAC  CCC  ATT  GCC  TGT  GGC  ATG  GAT  GAC  AAG        384
```

| | | Pro | Leu | Glu<br>115 | Pro | Gly | Pro | Tyr | Pro<br>120 | Ile | Ala | Cys | Gly | Met<br>125 | Asp | Asp | Lys | |
|---|---|---|---|---|---|---|---|---|---|---|---|---|---|---|---|---|---|---|

```
GCA TCG GGT TTG GAC GAG CAG CAG ACA GTG TTC TAC AAT TCT GTG AAG         432
Ala Ser Gly Leu Asp Glu Gln Gln Thr Val Phe Tyr Asn Ser Val Lys
    130             135                 140

ACC GGC TAC ACC ATC GGC TAC AGC TTG TCC CTC GCC GCC CTC CTG GTC         480
Thr Gly Tyr Thr Ile Gly Tyr Ser Leu Ser Leu Ala Ala Leu Leu Val
145             150                 155                 160

GCC ACC GCC ATC TTG AGC CTG TTC AGG AAG CTC CAC TGC ACT CGG AAC         528
Ala Thr Ala Ile Leu Ser Leu Phe Arg Lys Leu His Cys Thr Arg Asn
                165                 170                 175

TAC ATC CAC ATG CAC CTC TTC ATA TCC TTC ATC CTG AGG GCC ACC GCC         576
Tyr Ile His Met His Leu Phe Ile Ser Phe Ile Leu Arg Ala Thr Ala
            180                 185                 190

GTC TTC ATC AAA GAC TTG GCC CTC TTC GAC AGC GAG GAA TCA GAC CAC         624
Val Phe Ile Lys Asp Leu Ala Leu Phe Asp Ser Glu Glu Ser Asp His
        195                 200                 205

TGC TCC AAG GGC TCG GTG GGC TGT AAG GCA GCC GTG GTT TTA TTC CAG         672
Cys Ser Lys Gly Ser Val Gly Cys Lys Ala Ala Val Val Leu Phe Gln
    210                 215                 220

TAC TGT GTC ATG GCC AAC TTC TTC TGG CTG CTG GTG GAG GGC CTC TAC         720
Tyr Cys Val Met Ala Asn Phe Phe Trp Leu Leu Val Glu Gly Leu Tyr
225                 230                 235                 240

CTG CAC ACC CTA CTT GCC GTG TCC TTC TTC TCT GAG CGG AAG TAC TTC         768
Leu His Thr Leu Leu Ala Val Ser Phe Phe Ser Glu Arg Lys Tyr Phe
                245                 250                 255

TGG GGG TAC ATA TTC GTC GGC TGG GGG GTG CCC AGC ACC TTC ATC ATG         816
Trp Gly Tyr Ile Phe Val Gly Trp Gly Val Pro Ser Thr Phe Ile Met
            260                 265                 270

GTG TGG ACC GTC GTC AGA ATC CAT TTT GAG GAT TAT GGA TGC TGG GAC         864
Val Trp Thr Val Val Arg Ile His Phe Glu Asp Tyr Gly Cys Trp Asp
        275                 280                 285

ACC ATC CAC TCC TCA CTG TGG TGG ATC ATA AAG GCC CCC ATC CTC GCC         912
Thr Ile His Ser Ser Leu Trp Trp Ile Ile Lys Ala Pro Ile Leu Ala
    290                 295                 300

TCC ATC CTG GTG AAC TTC ATC CTA TTC ATT CGC ATC ATC GGA ATC TTG         960
Ser Ile Leu Val Asn Phe Ile Leu Phe Ile Arg Ile Ile Gly Ile Leu
305                 310                 315                 320

GTT CAG AAA CTG CGA CCC CCA GAT GTC GGG AAG AGT GAC AAC AGC CCA        1008
Val Gln Lys Leu Arg Pro Pro Asp Val Gly Lys Ser Asp Asn Ser Pro
                325                 330                 335

TAC TCG AGA CTA GCC AAG TCC ACT CTT CTG CTG ATC CCC TTA TTT GGA        1056
Tyr Ser Arg Leu Ala Lys Ser Thr Leu Leu Leu Ile Pro Leu Phe Gly
            340                 345                 350

GTG CAC TAC ATC ATG TTT GCC TTC TTC CCT GAC AAT TTT AAG GCC GAA        1104
Val His Tyr Ile Met Phe Ala Phe Phe Pro Asp Asn Phe Lys Ala Glu
        355                 360                 365

GTG AAA ATG GTC TTT GAG CTC ATC GTG GGA TCT TTC CAG GGT TGT GTG        1152
Val Lys Met Val Phe Glu Leu Ile Val Gly Ser Phe Gln Gly Cys Val
    370                 375                 380

GTG GCC ATC CTC TAC TGC TTC CTC AAT GGT GAG GTG CAG GCA GAG CTG        1200
Val Ala Ile Leu Tyr Cys Phe Leu Asn Gly Glu Val Gln Ala Glu Leu
385                 390                 395                 400

CGG CGG AAG TGG CGG CGC TGG CAC CAG CAG GGC GTC TTG GGC TGG GAC        1248
Arg Arg Lys Trp Arg Arg Trp His Gln Gln Gly Val Leu Gly Trp Asp
                405                 410                 415

TCC AAA TAC CAG CAC CCG TCA GGA GGC AGC AAC GGG GAC ACG TGC AGC        1296
Ser Lys Tyr Gln His Pro Ser Gly Gly Ser Asn Gly Asp Thr Cys Ser
            420                 425                 430

ACG CAG GTC TCC ATG CTG ACC CGT GTC AGC CCC AGT GCG CGC CGC TCC        1344
```

```
Thr Gln Val Ser Met Leu Thr Arg Val Ser Pro Ser Ala Arg Arg Ser
        435                 440                 445

TCC AGC TTC CAG GCC GAA GTC TCC CTG GTC TGA                              1377
Ser Ser Phe Gln Ala Glu Val Ser Leu Val
    450                 455
```

(2) INFORMATION FOR SEQ ID NO:2:

(i) SEQUENCE CHARACTERISTICS:
        (A) LENGTH: 458 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Pro Leu Ser Pro Pro Pro Ala Gly Trp Phe Cys Val Leu Ala
 1               5                  10                      15

Gly Val Leu Ala Cys Val Leu Gly Pro Val Gly Ser Trp Ala Val Gly
             20                  25                  30

Leu Gln Gln Glu Glu Cys Asp Tyr Leu Gln Met Ile Lys Val Gln His
             35                  40                  45

Lys Gln Cys Leu Glu Glu Ala Gln Leu Glu Asn Glu Thr Ser Gly Cys
         50                  55                  60

Ser Lys Met Trp Asp Asn Leu Thr Cys Trp Pro Ala Thr Pro Arg Gly
 65                  70                  75                  80

Gln Val Val Val Leu Ala Cys Pro Leu Ile Phe Lys Leu Phe Ser Pro
                 85                  90                  95

Thr Gln Gly Leu Asn Val Ser Arg Asn Cys Thr Asp Glu Gly Trp Thr
                100                 105                 110

Pro Leu Glu Pro Gly Pro Tyr Pro Ile Ala Cys Gly Met Asp Asp Lys
            115                 120                 125

Ala Ser Gly Leu Asp Glu Gln Gln Thr Val Phe Tyr Asn Ser Val Lys
        130                 135                 140

Thr Gly Tyr Thr Ile Gly Tyr Ser Leu Ser Leu Ala Ala Leu Leu Val
145                 150                 155                 160

Ala Thr Ala Ile Leu Ser Leu Phe Arg Lys Leu His Cys Thr Arg Asn
                165                 170                 175

Tyr Ile His Met His Leu Phe Ile Ser Phe Ile Leu Arg Ala Thr Ala
                180                 185                 190

Val Phe Ile Lys Asp Leu Ala Leu Phe Asp Ser Glu Glu Ser Asp His
            195                 200                 205

Cys Ser Lys Gly Ser Val Gly Cys Lys Ala Ala Val Val Leu Phe Gln
        210                 215                 220

Tyr Cys Val Met Ala Asn Phe Phe Trp Leu Leu Val Glu Gly Leu Tyr
225                 230                 235                 240

Leu His Thr Leu Leu Ala Val Ser Phe Phe Ser Glu Arg Lys Tyr Phe
                245                 250                 255

Trp Gly Tyr Ile Phe Val Gly Trp Gly Val Pro Ser Thr Phe Ile Met
                260                 265                 270

Val Trp Thr Val Val Arg Ile His Phe Glu Asp Tyr Gly Cys Trp Asp
            275                 280                 285

Thr Ile His Ser Ser Leu Trp Trp Ile Ile Lys Ala Pro Ile Leu Ala
        290                 295                 300

Ser Ile Leu Val Asn Phe Ile Leu Phe Ile Arg Ile Ile Gly Ile Leu
305                 310                 315                 320

Val Gln Lys Leu Arg Pro Pro Asp Val Gly Lys Ser Asp Asn Ser Pro
```

|  |  |  | 325 |  |  |  |  | 330 |  |  |  |  | 335 |  |
|---|---|---|---|---|---|---|---|---|---|---|---|---|---|---|
| Tyr | Ser | Arg | Leu | Ala | Lys | Ser | Thr | Leu | Leu | Leu | Ile | Pro | Leu | Phe | Gly |
|  |  |  | 340 |  |  |  |  | 345 |  |  |  |  | 350 |  |
| Val | His | Tyr | Ile | Met | Phe | Ala | Phe | Phe | Pro | Asp | Asn | Phe | Lys | Ala | Glu |
|  |  |  | 355 |  |  |  |  | 360 |  |  |  |  | 365 |  |
| Val | Lys | Met | Val | Phe | Glu | Leu | Ile | Val | Gly | Ser | Phe | Gln | Gly | Cys | Val |
|  |  | 370 |  |  |  |  | 375 |  |  |  |  | 380 |  |  |
| Val | Ala | Ile | Leu | Tyr | Cys | Phe | Leu | Asn | Gly | Glu | Val | Gln | Ala | Glu | Leu |
| 385 |  |  |  |  | 390 |  |  |  |  | 395 |  |  |  |  | 400 |
| Arg | Arg | Lys | Trp | Arg | Arg | Trp | His | Gln | Gln | Gly | Val | Leu | Gly | Trp | Asp |
|  |  |  |  | 405 |  |  |  |  | 410 |  |  |  |  | 415 |  |
| Ser | Lys | Tyr | Gln | His | Pro | Ser | Gly | Gly | Ser | Asn | Gly | Asp | Thr | Cys | Ser |
|  |  |  | 420 |  |  |  |  | 425 |  |  |  |  | 430 |  |
| Thr | Gln | Val | Ser | Met | Leu | Thr | Arg | Val | Ser | Pro | Ser | Ala | Arg | Arg | Ser |
|  |  | 435 |  |  |  |  | 440 |  |  |  |  | 445 |  |  |
| Ser | Ser | Phe | Gln | Ala | Glu | Val | Ser | Leu | Val |  |  |  |  |  |  |
|  |  | 450 |  |  |  | 455 |  |  |  |  |  |  |  |  |  |

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTGCACCTCA CCATTGAGGA AGCAGTA                    27

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TTCCGGAGGC TGCAYTGCAC YCGMAACTAC AT            32

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTAAAACGAC GGCCAGT                            17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CAGGAAACAG CTATGAC                                                                                      17

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AGCTTACCGG TG                                                                                           12

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCGACACCGG TA                                                                                           12